US011478176B2

(12) United States Patent
Lee et al.

(10) Patent No.: US 11,478,176 B2
(45) Date of Patent: Oct. 25, 2022

(54) MINIATURE AND INTELLIGENT URINE SENSING SYSTEM

(71) Applicant: National Cheng Kung University, Tainan (TW)

(72) Inventors: Shuenn-Yuh Lee, Tainan (TW); Ju-Yi Chen, Tainan (TW); Meng-Dar Shieh, Tainan (TW); Chia-Yu Lin, Tainan (TW); Yu-Jin Lin, Changhua County (TW); Ding-Siang Ciou, Kaohsiung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 425 days.

(21) Appl. No.: 16/697,216

(22) Filed: Nov. 27, 2019

(65) Prior Publication Data

US 2021/0113131 A1    Apr. 22, 2021

(30) Foreign Application Priority Data

Oct. 18, 2019 (TW) ................................. 108137775

(51) Int. Cl.
*A61B 5/20* (2006.01)
*G01N 33/493* (2006.01)
(Continued)

(52) U.S. Cl.
CPC ............ *A61B 5/207* (2013.01); *A61B 5/0022* (2013.01); *A61B 5/201* (2013.01); *A61B 5/4842* (2013.01);
(Continued)

(58) Field of Classification Search
CPC ....... A61B 5/207; A61B 5/0022; A61B 5/201; A61B 5/4842; A61B 2562/028; A61B 2562/245; A61B 10/007; A61B 5/14507; A61B 5/208; A61B 5/14546; G16H 50/30; G16H 40/67; G16H 80/00; G01N 33/493; G01N 1/20; G01N 2800/325;
(Continued)

(56) References Cited

U.S. PATENT DOCUMENTS

| 2007/0179389 A1* | 8/2007 | Wariar | A61B 5/002 |
| | | | 600/513 |
| 2017/0238911 A1* | 8/2017 | Duval | A61B 5/207 |

(Continued)

*Primary Examiner* — Alex M Valvis
*Assistant Examiner* — Chanel J Jhin
(74) *Attorney, Agent, or Firm* — Chun-Ming Shih; Lanway IPR Services

(57) ABSTRACT

In a microrunner structure, there are provided with components for a cleaning procedure required to conduct electrochemical sensing when a biosensor is activated for sensing; and a urine signal detection device that is a SoC (System on a Chip), which has a wireless transceiving circuit for receiving a urine measurement method and channel information transmitted from an intelligent device, and in turn, outputting a stimulus signal to trigger a biosensor or a non-biosensor in a multi-channel structure to conduct urine sense processing for a sensing area, as well as transmitting detection processing for a concentration of urine substances from the electrochemical sensing to the intelligent device through the wireless transceiving circuit to assess a risk index between a heart disease or diabetes and a kidney disease.

8 Claims, 7 Drawing Sheets

(51) Int. Cl.
*G16H 50/30* (2018.01)
*A61B 5/00* (2006.01)

(52) U.S. Cl.
CPC ........... *G01N 33/493* (2013.01); *G16H 50/30* (2018.01); *A61B 2562/028* (2013.01); *A61B 2562/245* (2013.01)

(58) Field of Classification Search
CPC .. G01N 2800/347; G01N 33/68; G01N 33/70; A47K 13/24
USPC .......................................................... 600/345
See application file for complete search history.

(56) References Cited

U.S. PATENT DOCUMENTS

2018/0149612 A1* 5/2018 Kumar ............... A61B 5/14507
2018/0263826 A1* 9/2018 Staton ................ A61B 5/14507
2019/0298317 A1* 10/2019 Colgan ................ A61B 5/207

\* cited by examiner

MINIATURE AND INTELLIGENT URINE SENSING SYSTEM

CROSS-REFERENCE TO RELATED APPLICATIONS

This application claims the priority of Taiwan Application No. 108137775 filed on Oct. 18, 2019, in the State Intellectual Property Office of the R.O.C., the disclosure of which is incorporated herein by reference.

BACKGROUND OF THE INVENTION

Field of the Invention

The invention relates to the field of urine detection, and in detail, refers to a miniature and intelligent urine sensing system with an integrated circuit combined with a urine sensor test piece for achieving miniaturization and a built-in wireless transceiving circuit for achieving IoT (Internet of Things) and cloud calculation and processing.

Descriptions of the Related Art

Most existing urine detection instruments are enzyme based sensors, which, in conjunction with optical detection, require long waiting time for detection results. Moreover, the volume of the detection instruments and equipments is quite large, such that the detection has to be conducted in a hospital or a test station. However, with the advancement of electronic technology, home self-detection devices that do not need professional operation already emerge. A home self-detection device is a handheld equipment, so that a user simply inserts electrodes of a urine detection test piece dipped with urine under test into the home self-detection device for the home self-detection device to perform interpretation and analysis.

However, the aforementioned urine detection test piece and handheld home self-detection device are still confined for concentration of data of urine of albumin, creatinine, cystatin C, NT-proBNP, troponin I, etc. under test in the urine be sensed because a single type of non-enzyme based structure or enzyme based structure is used for existing urine detection test pieces, and the detection circuit in the home self-detection device in the detection circuit also needs to operate in conjunction with a structure design of the urine detection test piece. That is, the adoption of an impedance based measurement is required for the home self-detection device if the urine detection test piece adopts the enzyme based structure, while a voltage or current based measurement detection circuit is adopted for the home self-detection device if the non-enzyme based structure is adopted for the urine detection test piece. Therefore, the home self-detection devices on the market are limited for use, resulting in poor generality. Furthermore, a home self-urine detection device still has a certain volume, and the urine detection test piece has to be carried in order to complete measurement of the concentration for certain substances in the urine, such that the use is quite inconvenient, especially for patients who lie on bed due to disease or patients who need to collect urine substance concentrations for long-term observation of health conditions.

Furthermore, although the concentration of certain substances in the urine may be obtained by the home self-urine detection device and the urine test piece mentioned above, since the user is often not a professional medical person, the obtained concentration of certain substances in the urine cannot be used to identify the symptom it represents immediately, such that the treatment might be delayed.

Therefore, it is a technical subject to be solved by the invention about how to provide a urine detection equipment which has a small volume for friendly use and is helpful for pathological interpretation, and may detect the concentration of various substances in the urine with a single urine detection test piece.

SUMMARY OF THE INVENTION

In view of the above drawbacks in the conventional technology, a primary object of the invention is used to provide a miniature and intelligent urine sensing system, which adopts a miniature design to fit to a detection operator for urine detection, and may transmit concentrations of various detected substances in the urine to the cloud in a wireless manner for data analysis.

Along another purpose of the invention, the miniature and intelligent urine sensing system according to the invention uses multi-channel urine detection test pieces without being limited to a single biosensor (such as an enzyme based sensor) or non-biosensor, and may acquire concentrations of more substances in the urine for analysis in order to provide a variety of substance sensing functions.

To achieve the above and other objects, a miniature and intelligent urine sensing system, which transmits and receives signals through a wireless transceiving technology and an intelligent device, the miniature and intelligent urine sensing system including: a urine sensor test piece having microrunner structures and multi-channel structures, each of the multi-channel structures being provided with a non-biosensor or a biosensor, wherein the microrunner structure is arranged with multiple micropumps, micromixers as well as waste chambers for accommodating waste liquids and electrolytic chambers for accommodating electrolyte solution therein, in order for the biosensor to conduct a cleaning procedure required for electrochemical sensing when being activated; the multi-channel structure being used for shunting a urine under test to form a sensing area; and a urine signal detection device having a power supply unit, a digital controller, a wireless transceiving circuit, a trigger processing unit and a sense signal processing unit, wherein the power supply unit, the digital controller, the wireless transceiving circuit, the trigger processing unit and the sense processing unit can be integrated into a System on a Chip (SoC), wherein the power supply unit is used for supplying power to the digital controller, the wireless transceiving circuit, the trigger processing unit and the sense signal processing unit, the wireless transceiving circuit is used for receiving a urine measurement method and channel information transmitted from the intelligent device and transmitting the urine measurement method and the channel information to the digital controller, and in turn, the trigger processing unit is driven to output a stimulus signal to trigger the biosensor or the non-biosensor in the multi-channel structure to conduct urine sense processing for the sensing area, and the sense signal processing unit conducts detection processing for a concentration of urine substances sensed by conducting electrochemical sensing with respect to the triggered biosensor and non-biosensor according to the urine measurement method and the channel information, followed by transmitting the concentration back to the digital controller, which transmits the concentration to the intelligent device through the transceiving circuit for assessing a risk index between a heart disease or diabetes and a kidney disease.

Preferably, in the miniature and intelligent urine sensing system said above, wherein the trigger processing unit includes: a voltage digital analog converter, a current digital analog converter, a sine wave generator and an output interface with multi-channel switching, the trigger processing unit is controlled by the digital controller, the output interface with multi-channel switching is connected with the microrunner structure and the multi-channel structure of the urine sensor test piece, in case a urine detection is conducted with the biosensor based on the urine measurement method and the channel information received by the digital controller, the sine wave generator in the trigger processing unit is driven for performing an impedance based measurement to adjust a sine wave output frequency range, adjust a sine wave output amplitude; or in case the urine detection is conducted with the non-biosensor based on the urine measurement method and the channel information received by the digital controller, the voltage digital analog converter or the current digital analog converter in the trigger processing unit is driven for conducting the urine detection, wherein a voltage based measurement is performed to adjust an output voltage, adjust output time, or a current based measurement is performed to adjust an output current, adjust output time, the digital controller drives the voltage, current or impedance measurement processing and collects electrochemical reactions on each of the structures on the urine sensor test piece by means of time division multiplexing through the output interface with multi-channel switching.

Preferably, in the miniature and intelligent urine sensing system said above, wherein the trigger processing unit is capable of feedback adjustments, when the digital controller drives the voltage digital analog converter, the current digital analog converter or the sine wave generator in the trigger processing unit to conduct the urine detection for the urine sensor test piece, a feedback adjustment output current is output to the current digital analog converter according to a sensed current value, a feedback adjustment output voltage is output to the voltage digital analog converter according to a sensed voltage value, or a feedback adjustment frequency and amplitude is output to the sine wave generator according to a sensed impedance value, thereby a correction of the urine sensor test piece is achieved.

Preferably, in the miniature and intelligent urine sensing system said above, wherein the sense signal processing unit includes: an analog to digital converter, an amplitude detector, a phase detector and an input interface with multi-channel switching, the analog to digital converter, the amplitude detector and the phase detector of the sense signal processing unit conduct sense processing with respect to the concentration of the urine substances detected by the electrochemical sensing for the triggered biosensor or the non-biosensor by means of time division multiplexing according to the selected measurement method and channel information through the input interface with multi-channel switching and transmit the concentration back to the digital controller.

Preferably, in the miniature and intelligent urine sensing system said above, wherein data with respect to urine substances required for assessing the risk index between the heart disease and the kidney disease are any one in the group composed of concentrations of albumin, creatinine, cystatin C, NT-proBNP and troponin I; furthermore, the above data with respect to urine substances required for assessing the risk index between the diabetes and the kidney disease are any one in the group composed of concentrations of transferrin, NAG (N-acetyl-β-D-glucosaminidase), type IV collagen, TNF-α and 8-OHdG (8-hydroxy-2'-deoxyguanosine).

Preferably, in the miniature and intelligent urine sensing system said above, wherein the urine sensor test piece and the urine signal detection device are integrated into a portable device, diapers, urine bags, underwear, toilets or urinals, for a user to conduct a urine detection anytime and anywhere.

Preferably, in the miniature and intelligent urine sensing system said above, wherein the miniature and intelligent urine sensing system conducts a message transmission with a cloud server database through the intelligent device to achieve an IoT (Internet of Things) capable service, the cloud server database has a built-in AI (artificial intelligence) algorithm, which includes: an early kidney disease risk assessment algorithm and a heart disease risk assessment algorithm, the algorithm calculates a degree of risk suffering from a heart disease based on concentrations of albumin, creatinine, cystatin C, NT-proBNP and troponin I in the urine detected by the urine signal detection device and assesses a risk of the heart disease and the kidney disease, as well as provides a result of the calculation or the assessment to medical personnel and users through an APP of the intelligent device; furthermore, the above the miniature and intelligent urine sensing system conducts a message transmission with a cloud server database through the intelligent device to achieve an IoT capable service, the cloud server database has a built-in AI (artificial intelligence) algorithm, which includes: an early kidney disease risk assessment algorithm and a diabetes disease risk assessment algorithm, the algorithm calculates a degree of risk suffering from a diabetes disease based on concentrations of transferrin, NAG (N-acetyl-β-D-glucosaminidase), type IV collagen, TNF-α, 8-OHdG (8-hydroxy-2'-deoxyguanosine), etc. in the urine detected by the urine signal detection device and assesses a risk of the diabetes disease and the kidney disease, as well as provides a result of the calculation or the assessment to medical personnel and users through an APP of the intelligent device.

In comparison to prior arts, the miniature and intelligent urine sensing system according to the invention allows the user to detect urine regularly without time and place constraints, and prevent from heart disease or diabetes through constant detection. At the same time, the invention also conduct transmission through a wireless transceiving circuit and a cloud platform to assess the risk of suffering from heart disease or diabetes through an AI (artificial intelligence) algorithm, and to provide to the user as a reference through a web page, an intelligent device APP. The invention may also be combined with products such as a portable device, diapers, urine bags, underwear, toilets or urinals, so that early screening of cardiovascular diseases or diabetes can be linked to home life and community screening more easily.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
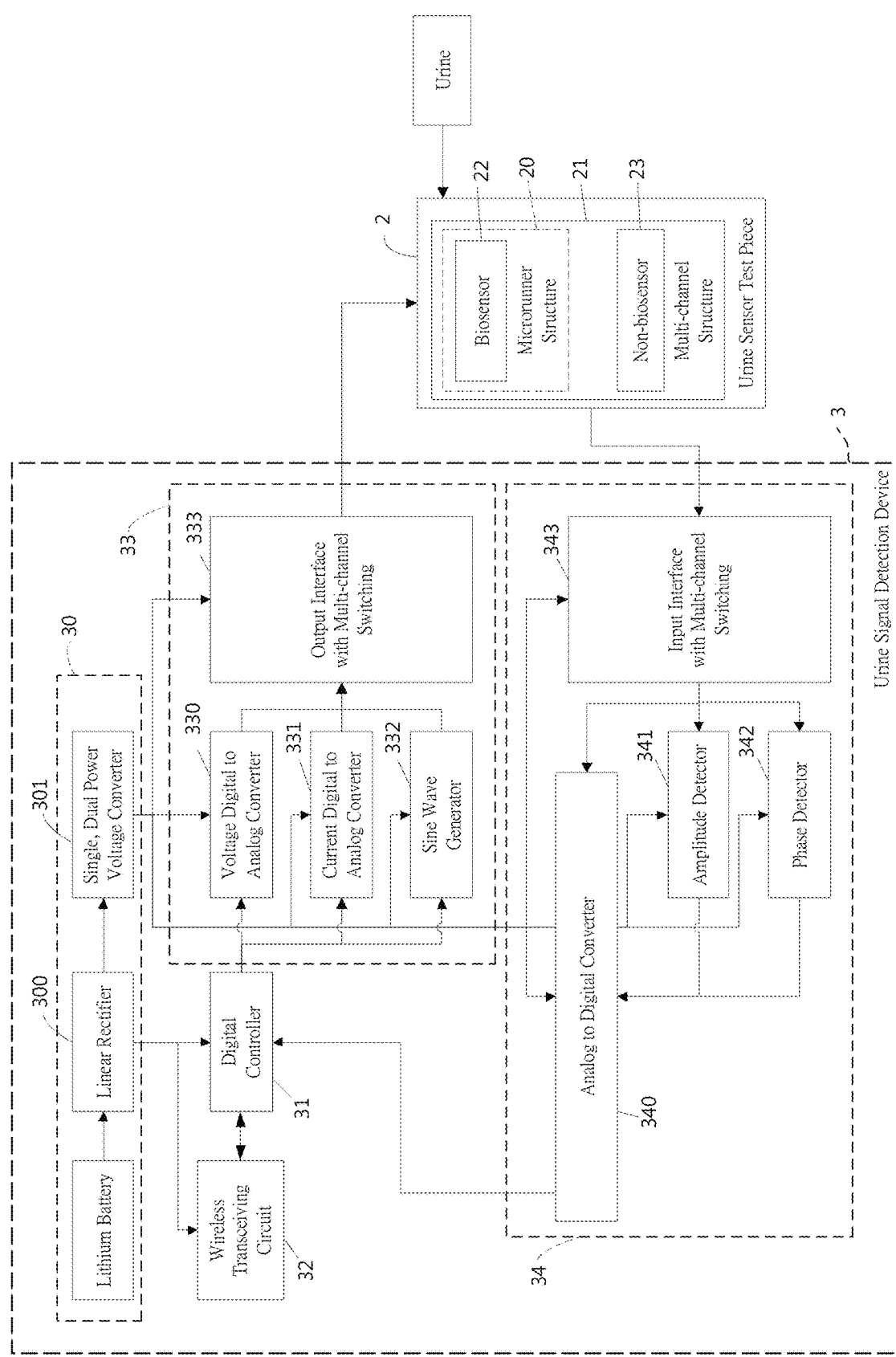
FIG. 1 is a block diagram showing a basic structure of a miniature and intelligent urine sensing system according to the invention.

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

As shown in FIG. 1, which illustrates a block diagram showing a basic architecture of a miniature and intelligent urine sensing system according to the invention, the miniature and intelligent urine sensing system 1 according to the invention including: a urine sensor test piece 2 and a urine signal detection device 3, the urine signal detection device 3 including: a power supply unit 30, a digital controller 31, a wireless transceiving circuit 32, a trigger processing unit 33 and a sense signal processing unit 34. The urine signal detection device 3 is implemented by a SoC (System on a Chip), which refers to an integrated circuit with a power supply unit 30, a digital controller 31, a wireless transceiving circuit 32, a trigger processing unit 33 and a sense processing unit 34 integrated into the urine signal detection device 3, thereby achieving miniaturization. The power supply unit 30 is used for supplying power to the digital controller 31, the wireless transceiving circuit 32, the trigger processing unit 33 and the sense signal processing unit 34. A linear rectifier 300 of the power supply unit 30 is used to rectify an input energy into a DC voltage lower than the input to conduct power supply processing for the digital controller 31, the wireless transceiving circuit 32, the trigger processing unit 33 and the sense signal processing unit 34. A single, dual power voltage converter 301 provides a single or dual power supply to the trigger processing unit 33 and the sense processing unit 34 according to chemical characteristics of a biosensor or a non-biosensor to be adopted by a urine sensor test piece 2, and the urine sensor test piece 2 uses three-electrode electrochemical sensing, wherein working electrodes, reference electrodes and counter electrodes are included, a constant potentiometer of the urine signal detection device 3 provides a potential required for an electrochemical reaction, an impedance detection circuit measures an impedance variation, that is, a current signal generated due to the electrochemical reaction, for the urine signal detection device 3 to treat a resistance variation, a voltage variation or a current variation caused by substance bonding of the urine under test to analyze a variety of substance sense processing, the concentrations of substances such as albumin, creatinine, cystatin C, NT-proBNP, troponin I, transferrin, NAG (N-acetyl-β-D-glucosaminidase), type IV collagen, TNF-α, 8-OHdG (8-hydroxy-2'-deoxyguanosine), and do signal processing and computation via a back-end equipment (e.g., an intelligent device or/and a cloud server database).

The urine sensor test piece 2 is a multi-substance sensor, which senses a variety of cardiovascular and kidney disease risk factors, has microrunner structures 20 and multi-channel structures 21, each of the multi-channel structures 21 is provided with a biosensor 22 and a non-biosensor 23, wherein the microrunner structure 20 is provided with multiple micropumps, micromixers, waste chambers for accommodating waste liquids and electrolytic chambers for accommodating electrolyte solution therein (not shown), and chamber openings of the waste chambers and the electrolytic chambers are provided with micro-gates in order for the biosensor 22 to conduct a cleaning procedure required for electrochemical sensing when being activated. The microrunner structure 20 may be provided with multiple micropumps, micromixers, waste chambers and electrolytic chambers therein. The multi-channel structure 21 is used for shunting the urine under test to form a sensing area. The biosensor 22 refers to a biosensing element (such as enzymes, antibodies and so on), which converts a variation amount for the urine under test into an electrical signal. The biosensor 22 includes structure designs such as antibody-antigen Immune type, aptamer primer modification, single-chain fv fragment, enzyme based sensor, etc. In addition, the biosensor 22 somewhat needs a secondary cleaning measurement variation amount, so that the micropumps and the micro-gates mentioned above are controlled by the urine signal detection device 3 digitally to open the electrolytic chambers for the accommodated electrolyte solution to clean the electrodes, and open the waste chamber to collect waste liquid, followed by conducting electrochemical sensing; the non-biosensor 23 is a sensor modified with non-biological sensing elements, including non-biosensors, electrocatalysts, molecular templates, ion sensors etc. The function for detecting concentrations of various sensed substances including albumin, creatinine, cystatin C, NT-proBNP and troponin I in the urine with a design structure of the urine sensor test piece 2 is available, so that a cloud equipment may perform a further calculation via the concentrations of substances to speculate the risk index of suffering from heart disease and kidney disease.

The miniature and intelligent urine sensing system 1 according to the invention is the multi-structure urine sensor test piece 2 in conjunction mentioned above. The trigger processing unit 33 and the sense processing unit 34 mentioned above provide a voltage detection, a current detection and an impedance detection to achieve sense processing of the biosensors and the non-biosensors, so that various substance sensing types for concentrations of substances including albumin, creatinine, cystatin C, NT-proBNP, troponin I, etc. in the urine mentioned above are available, as shown in FIG. 1, the trigger processing unit 33 includes: a voltage digital to analog converter 330, a current digital to analog converter 331, a sine wave generator 332 and an output interface with multi-channel switching 333, the trigger processing unit 33 is controlled by the digital controller 31, the sense signal processing unit 34 includes: an analog to digital converter 340, an amplitude detector 341 and a phase detector 342 and an input interface with multi-channel switching 343 and a processing signal is sent to the digital controller 31, which may conduct transmission and reception of signals with an external intelligent device (not shown here) through the wireless transceiving circuit 32. The intelligent device is, for example, a smartphone or a computer equipment etc.

Figure 2:
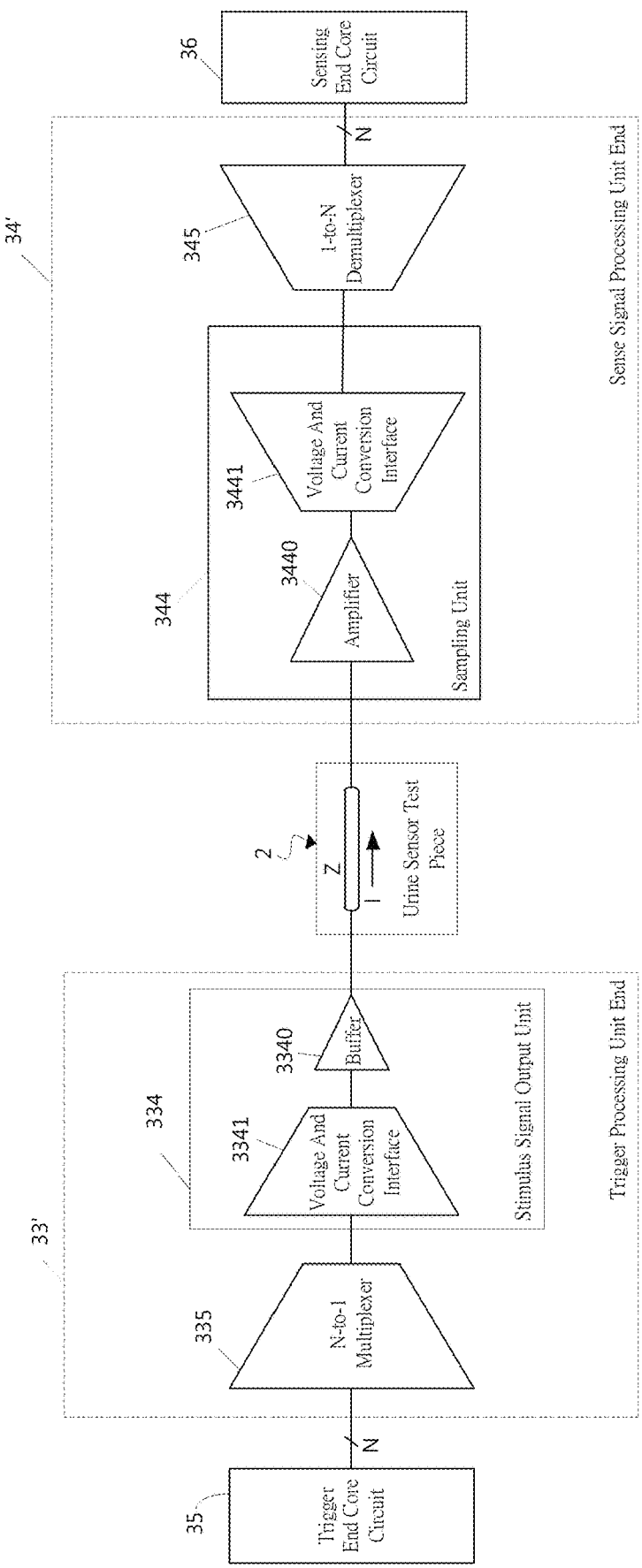
FIG. 2 is an embodiment showing an output interface and an input interface with multi-channel switching for a urine signal detection device of the miniature and intelligent urine sensing system according to the invention.

Next, refer to FIG. 2, which illustrates an embodiment of a trigger processing unit end 33' and a sense signal processing unit end 34' for the urine signal detection device of the miniature and intelligent urine sensing system according to the invention. Specifically, the trigger processing unit end 33' of this embodiment is a processing member of the urine signal detection device 3 for transmitting output signals, and the sense signal processing unit end 34' is a processing member of the urine signal detection device 3 for receiving input signals. For simplification of figures, a trigger end core circuit 35 shown in FIG. 2 is a processing circuit of the power supply unit 30, the digital controller 31, the wireless transceiving circuit 32, the voltage digital to analog converter 330, the current digital to analog converter 331, the sine wave generator 332, etc. of the urine signal detection device 3. The sensing end core circuit 36 is a processing circuit of the analog to digital converter 340, the amplitude detector 341 and the phase detector 342 of the urine signal detection device 3. The trigger processing unit end 33' of the urine signal detection device 3 includes an N-to-1 multiplexer 335 and a stimulus signal output unit 334, and the stimulus signal output unit 334 includes at least a buffer 3340 and a voltage and current conversion interface 3341. A channel structure to be triggered on the urine sensor test piece 2 is selected through the N-to-1 multiplexer 335, and the corresponding voltage detection, current detection or impedance detection is provided for the channel structure to be triggered to sense the concentration of a specific substance present in the urine under test. It is noted that there are multiple buffers 3340 and voltage and current conversion interfaces 3341 for the stimulus signal output unit 334. The voltage and current conversion interface 3341 may conduct a voltage to current conversion or a current to voltage conversion based on characteristics of the urine sensor test piece, providing a voltage or current stimulus to achieve serialized multiple parallel voltages or currents.

The sense signal processing unit end 34' of urine signal detection device 3 includes an 1-to-N demultiplexer 345, a sampling unit 344, while the sampling unit 344 includes at least an amplifier 3440 and a voltage and current conversion interface 3441. The amplifier 3440 is a signal amplifier and may restore a signal to a signal level of a voltage or current required for the sensing end core circuit 36 through the voltage and current conversion interface 3441.

The sensing end core circuit 36 conducts corresponding signal processing for a sense signal measured by the urine sensor test piece 2 to obtain substance characteristics present in the urine under test, while the sensing end core circuit 36 divides the sense signal into gain (|Z|) and phase (Φ) portions with respect to the signal processing for the sense signal to conduct detection, which may facilitate to restore the substance characteristics present in the urine under test and restore the impedance indicative of the substance characteristics. Moreover, prior to the detection, a minor stimulus signal (e.g., an AC electrical signal I) is injected to a sensing area of the urine sensor test piece 2 by the trigger end core circuit 35, and according to the principle of Ohm's law, the sense signal processing unit end 34' and the sensing end core circuit 36 may sense an impedance Z for the substance characteristics, such as the signal amplitude and phase of the detection signal, in the urine under test, present on the sensing area of the urine sensor test piece 2. It is to be noted additionally that the aforementioned minor AC signal may be, for example, a current, voltage, or charge. It is also noted that the amplitude of the sensing end core circuit 36 may be a voltage or current to achieve the detection of the voltage or current.

Figure 3:
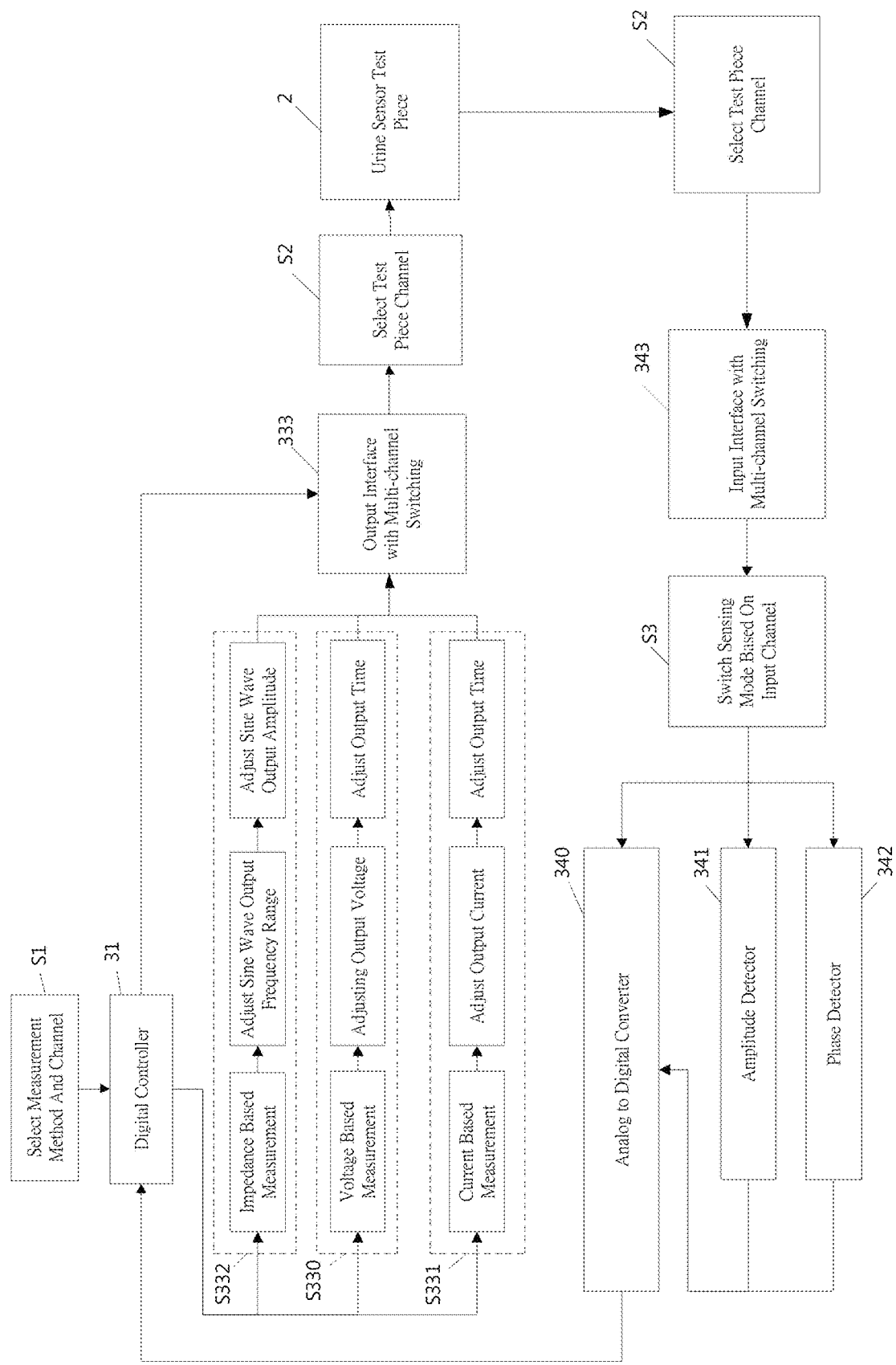
FIG. 3 is a flow chart showing sense processing for concentrations of urine substances conducted by the miniature and intelligent urine sensing system according to the invention receiving a selection instruction transmitted from an intelligent device for a urine sensor test piece.

A general operation situation is as shown in FIG. 3. First of all, step S1 is conducted. A user enters a desired measurement method and channel information through a smartphone, which are transmitted to the digital controller 31 by the wireless transceiving circuit 32 of the urine signal detection device 3 to drive the trigger processing unit 33 for sense processing of urine.

If the user selects to conduct a urine detection with a biosensor, then the digital controller 31 drives the sine wave generator 332 in the trigger processing unit 33 to perform the operation, that is, to perform an impedance based measurement in step S332 as shown in FIG. 3, thereby adjusting the sine wave output frequency range, adjusting the sine wave output amplitude. On the contrary, if the user selects to conduct the urine detection with a non-biosensor, then the digital controller 31 drives a voltage digital to analog converter 330 or a current digital to analog converter 331 in the trigger processing unit 33 to conduct a urine detection, that is, to perform a voltage based measurement in step S330 as shown in FIG. 3, thereby adjusting an output voltage, adjusting output time. Further, a current based measurement in step S331 as shown in FIG. 3 may be performed, adjusting an output current, adjusting output time. Moreover, the adoption of the aforementioned voltage digital to analog converter 330 or current digital to analog converter 331 is related to electrochemical characteristics of the urine sensor test piece 2. The digital controller 31 collects electrochemical reactions on each induction area on the urine sensor test piece 2 by means of time division multiplexing through the output interface 333 with multi-channel switching while driving the aforementioned voltage, current or impedance measurement processing, as shown in Step S2 of FIG. 3.

Then, as shown in Step S3 of FIG. 3, an analog to digital converter 340, an amplitude detector 341 and a phase detector 342 of the sense signal processing unit 34 conduct sense processing of concentration signals including albumin, creatinine, cystatin C, NT-proBNP and troponin I in the urine for each induction area (induction channel) on the urine sensor test piece 2 by means of time division multiplexing according to a selected test piece channel through the input interface with multi-channel switching 343, and transmit the concentration signal back to the digital controller 31.

As can be seen from FIG. 1 and FIG. 3, the urine sensor test piece 2 of the miniature and intelligent urine sensing system 1 according to the invention adopts microrunner and miniature sensor designs, in conjunction with a wireless transceiving function together with the urine signal detection device 3 designed as an integrated circuit, to achieve the effects of miniaturization and low power consumption, and can be further packaged into a portable or carry-on based urine detection product directly, by way as an example, may be integrated into a portable device, diaper, urine bag or underwear product, allowing for a user to conduct urine detection anytime and anywhere, and even more, may be combined with a toilet or a urinal, and thus upgraded to be an intelligent toilet or an intelligent urinal, etc. For items of urine detection nowadays, most items are for kidney disease warning. When kidney issues are found, the end stage of cardiovascular disease is usually reached, so that those items can only be used for reminder treatment, and cannot be used for conducting a preventive treatment at the early stage. However, the miniature and intelligent urine sensing system 1 according to the invention can be suitable for users of all ages to conduct large-scale, rapid, early prediction of heart disease and kidney disease, and can really reduce the number of people suffering from heart disease and kidney disease, improving the quality of national health.

Figure 4:
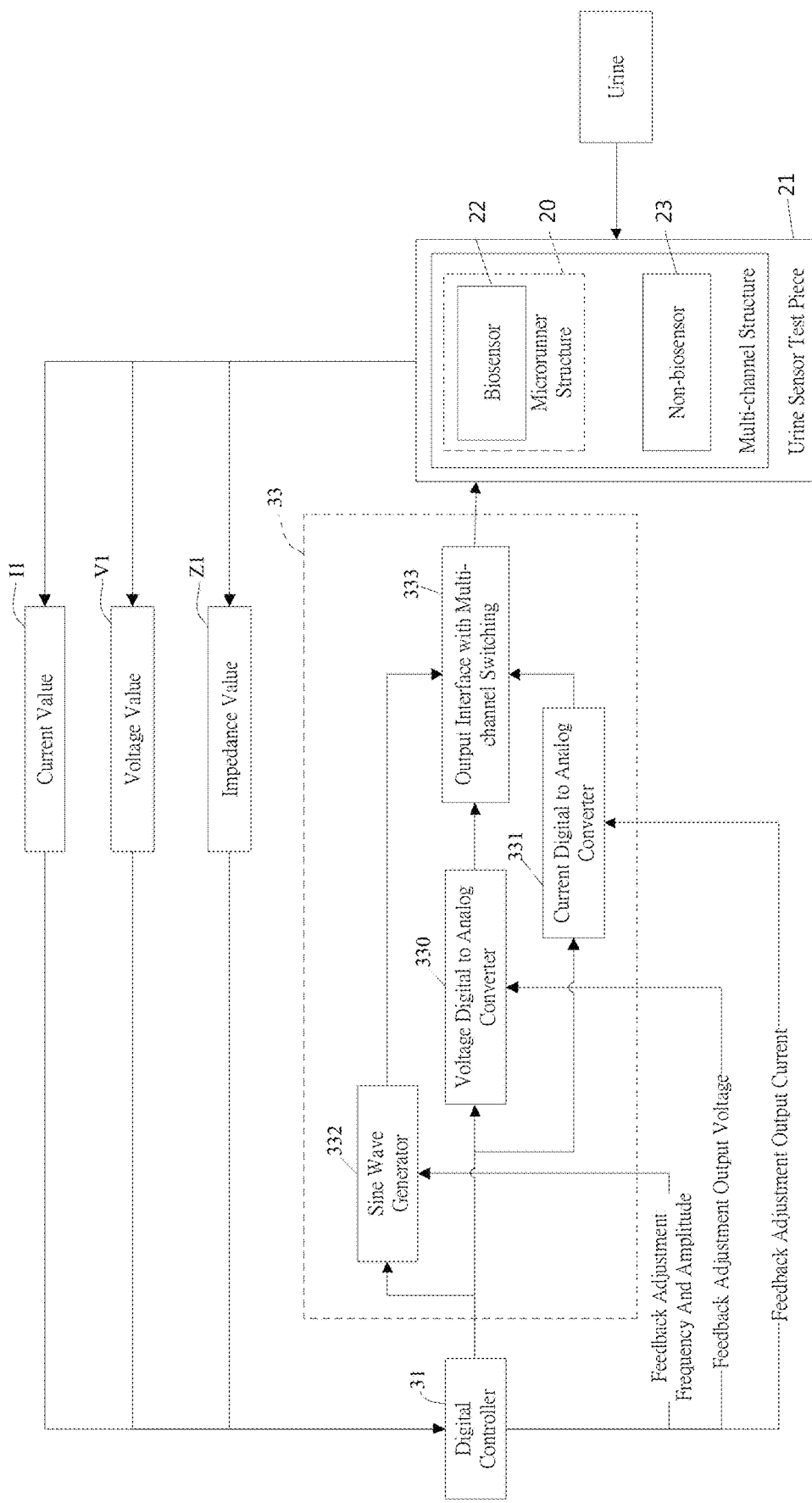
FIG. 4 is a functional block diagram showing a trigger processing unit of the miniature and intelligent urine sensing system according to the invention.

In addition, the trigger processing unit 33 of the miniature and intelligent urine sensing system 1 according to the invention is also capable of feedback adjustment. As shown in FIG. 4, because the urine sensor test piece 2 is designed with a chemical reaction, the characteristics of each test piece are not completely consistent and variability exists. Therefore, when the digital controller 31 drives the voltage digital to analog converter 330, the current digital to analog converter 331 or the sine wave generator 332 in the trigger processing unit 33 to conduct a urine detection for the urine sensor test piece 2, a feedback adjustment output current will be output to the current digital to analog converter 331 according to a sensed current value I1, a feedback adjustment output voltage will be output to the voltage digital to analog converter 330 according to a sensed voltage value V1, or a feedback adjustment frequency and amplitude will be output to the sine wave generator 332 according to a sensed impedance value Z1, thereby achieving a correction of the urine sensor test piece 2.

Figure 5A:
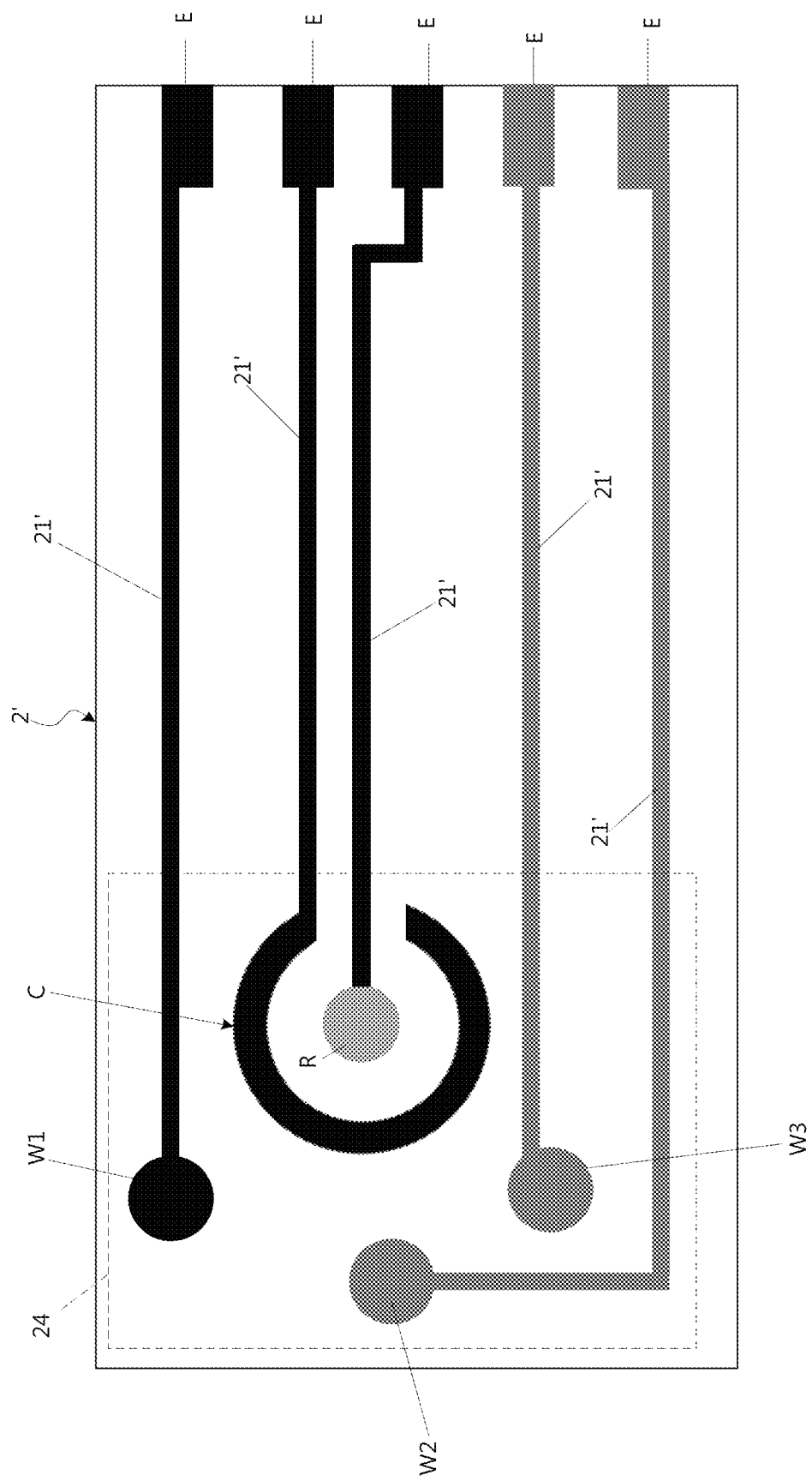
FIGS. 5A and 5B are a schematic view showing a structure of a urine sensor test piece in the miniature and intelligent urine sensing system according to the invention, and a schematic view showing the electrical connection between the urine sensor test piece and a urine signal detection device, respectively.
Figure 5B:
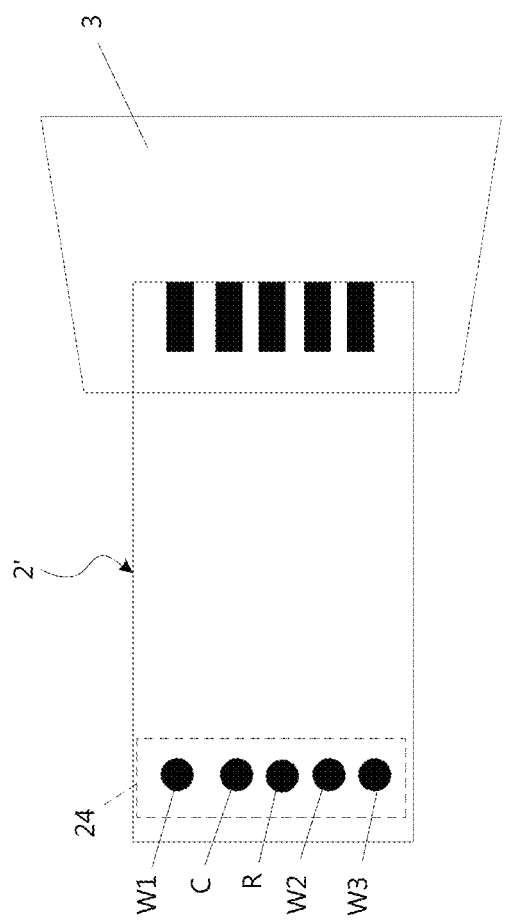

Furthermore, the design of microrunner structure mentioned above may also be discarded for the urine sensor test piece in the miniature and intelligent urine sensing system according to the invention, as shown in FIGS. 5A and 5B. The urine sensor test piece 2 of this embodiment may have catalytic active substances required for formation of biosensors or non-biosensors modified thereon by using an electrodeposition. As mentioned above, when the urine under test has stayed on an area under test 24 of the urine sensor test piece 2' for a period of time (e.g., about 30 minutes or 1 hour), the user conducts cleaning on the area under test with a clean water, followed by dropping an electrolyte solution on the area under test for the electrolyte solution to contact with working electrodes (W1, W2, W3), a reference electrode R and a counter electrode C on the area under test 24 for conducting electrochemical sensing. Moreover, the sensing results are provided to the urine signal detection device 3 through a contact electrode E by multi-channels 21' in respective connection with the working electrodes, the reference electrode and the counter electrode for sense signal processing. It is noted here additionally that the quantities of the urine sensor test pieces 2' and the working electrodes in this embodiment are not limited to three, but may be smaller or larger, the quantities are increased or decreased depending on the quantity of the urine substances to be sensed by the urine sensor test piece.

Figure 6:
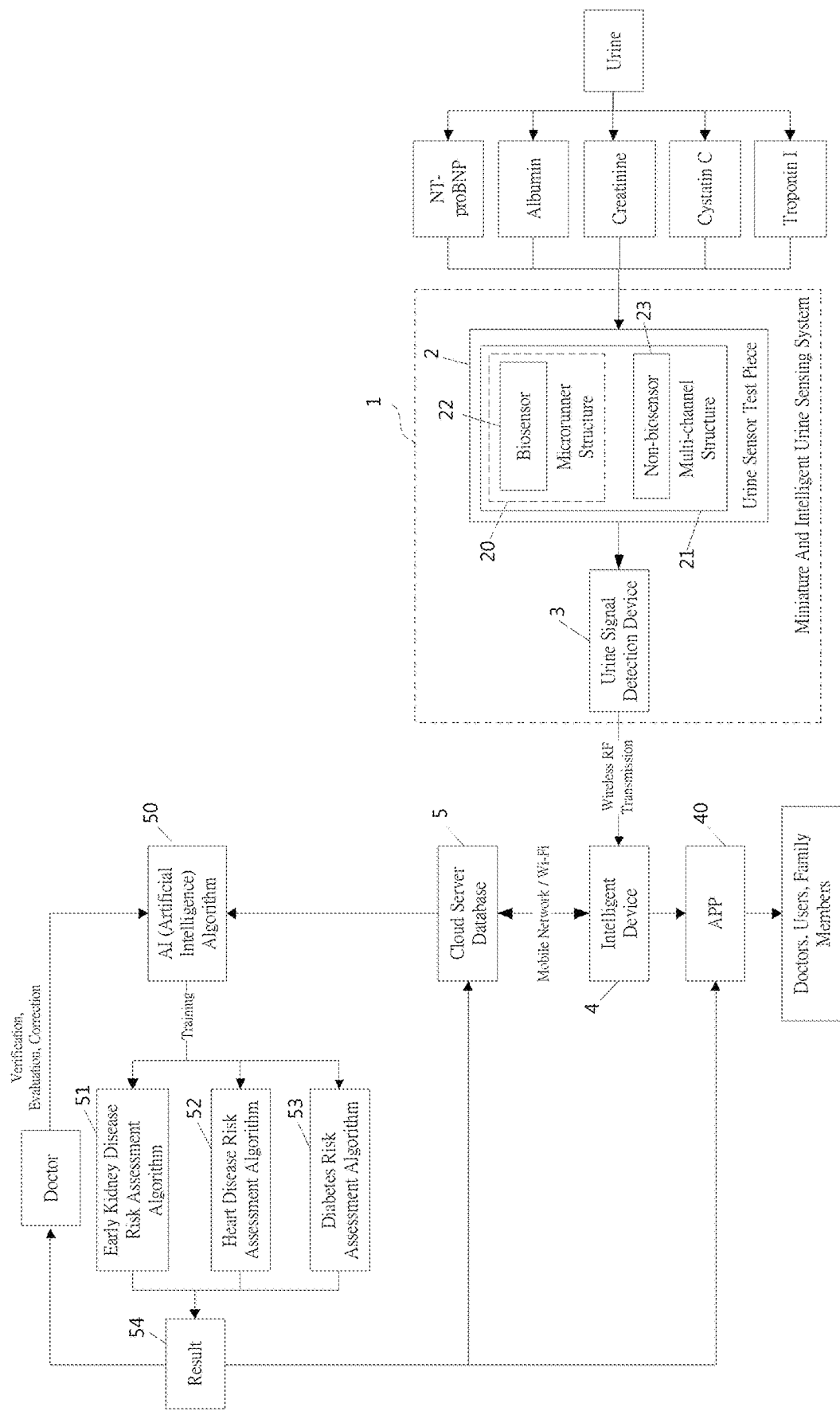
FIG. 6 is a conceptual diagram showing a basic architecture in which the miniature and intelligent urine sensing system according to the invention conducts a message transmission through an intelligent device and a cloud platform to implement an IoT capable service.

Next, refer to FIG. 6, which illustrates a conceptual diagram showing a basic architecture in which the miniature and intelligent urine sensing system according to the invention conducts a messages transmission through an intelligent device and a cloud platform to implement an IoT capable service, like a built-in AI algorithm 50 of a cloud server database 5 as shown in FIG. 6, the AI algorithm includes: an early kidney disease risk assessment algorithm 51 and a heart disease risk assessment algorithm 52, mainly used to calculate a degree of risk suffering from a heart disease based on concentrations of albumin, creatinine, cystatin C, NT-proBNP and troponin I in the urine detected by the urine signal detection device 3 and assess a risk of the heart disease and the kidney disease, as well as provide a result 54 of the calculation or the assessment to medical personnel and users through an APP 40 of an intelligent device 4 or a computer APP for medical examination and home care.

In addition, the urine sensor test piece of the miniature and intelligent urine sensing system according to the invention has multi-channel structures, each of which is provided with respective biosensors or non-biosensors, so that there may be more types of urine substances that may be sensed, the more types of urine substances are including albumin, creatinine, cystatin C, NT-proBNP, troponin I and also including transferrin, NAG (N-acetyl-$\beta$-D-glucosaminidase), type IV collagen, TNF-$\alpha$, 8-OHdG (8-hydroxy-2'-deoxyguanosine), etc. Moreover, the AI algorithm 50 shown in FIG. 6 may also include: a diabetes risk assessment algorithm 53, which may assess a risk index between diabetes and kidney disease based on the concentrations of the substances.

In addition, with the interaction between transmission processing of the wireless transceiving circuit and the cloud server database 5, the miniature and intelligent urine sensing system 1 according to the invention may record, analyze urine detection logs of a user at any time, and provide long-term, multitude of and objective urine detection data to a doctor as a reference for auxiliary diagnosis when the user visits the doctor.

The examples above are only illustrative to explain principles and effects of the invention, but not to limit the invention. It will be apparent to those skilled in the art that modifications and variations can be made without departing from the scope of the invention. Therefore, the protection range of the rights of the invention should be as defined by the appended claims.

What is claimed is:

1. A miniature and intelligent urine sensing system, which transmits and receives signals through a wireless transceiving technology and an intelligent device, the miniature and intelligent urine sensing system comprising:
   a urine sensor test piece having a sensor, used for shunting a urine under test to form a sensing area; and
   a urine signal detection device having a power supply unit, a digital controller, a wireless transceiving circuit, a trigger processing unit and a sense signal processing unit, wherein the power supply unit, the digital controller, the wireless transceiving circuit, the trigger processing unit and the sense processing unit are integrated into a System on a Chip (SoC), wherein the power supply unit is used for supplying power to the digital controller, the wireless transceiving circuit, the trigger processing unit and the sense signal processing unit, the wireless transceiving circuit is used for receiving a urine measurement method and channel information transmitted from the intelligent device and transmitting the urine measurement method and the channel information to the digital controller, and in turn, the trigger processing unit is driven to output a stimulus signal to trigger the sensor to conduct urine sense processing for the sensing area through an electrical connection between the urine sensor test piece and the urine signal detection device, and the sense signal processing unit conducts detection processing for a concentration of urine substances sensed by conducting electrochemical sensing with respect to the triggered sensor according to the urine measurement method and the channel information, followed by transmitting the concentration back to the digital controller, which transmits the concentration to the intelligent device through the transceiving circuit for assessing a risk index between a heart disease or diabetes and a kidney disease.

2. The miniature and intelligent urine sensing system as claimed in claim 1, wherein the trigger processing unit comprises: a voltage digital analog converter, a current digital analog converter, a sine wave generator and an output interface, the trigger processing unit is controlled by the digital controller, the output interface is connected with the urine sensor test piece, in case a urine detection is conducted with the sensor based on the urine measurement method and the channel information received by the digital controller, the sine wave generator in the trigger processing unit is driven for performing an impedance based measurement to adjust a sine wave output frequency range, adjust a sine wave output amplitude; or in case the urine detection is conducted with the sensor based on the urine measurement method and the channel information received by the digital controller, the voltage digital analog converter or the current digital analog converter in the trigger processing unit is driven for conducting the urine detection, wherein a voltage based measurement is performed to adjust an output voltage, adjust output time, or a current based measurement is performed to adjust an output current, adjust output time, the digital controller drives the voltage, current or impedance measurement processing and collects electrochemical reactions on the urine sensor test piece through the output interface.

3. The miniature and intelligent urine sensing system as claimed in claim 2, wherein the trigger processing unit is capable of feedback adjustments, when the digital controller drives the voltage digital analog converter, the current digital analog converter or the sine wave generator in the trigger processing unit to conduct the urine detection for the urine sensor test piece, a feedback adjustment output current is output to the current digital analog converter according to a sensed current value, a feedback adjustment output voltage is output to the voltage digital analog converter according to a sensed voltage value, or a feedback adjustment frequency and amplitude is output to the sine wave generator according to a sensed impedance value, thereby a correction of the urine sensor test piece is achieved.

4. The miniature and intelligent urine sensing system as claimed in claim 1, wherein the sense signal processing unit comprises: an analog to digital converter, an amplitude detector, a phase detector and an input interface, the analog to digital converter, the amplitude detector and the phase detector of the sense signal processing unit conduct sense processing with respect to the concentration of the urine substances detected by the electrochemical sensing for the triggered sensor according to the selected measurement method and channel information through the input interface and transmit the concentration back to the digital controller.

5. The miniature and intelligent urine sensing system as claimed in claim 1, wherein data with respect to urine substances required for assessing the risk index between the heart disease and the kidney disease are any one in the group composed of concentrations of albumin, creatinine, cystatin C, NT-proBNP and troponin I.

6. The miniature and intelligent urine sensing system as claimed in claim 1, wherein data with respect to urine substances required for assessing the risk index between the diabetes and the kidney disease are any one in the group composed of concentrations of transferrin, N-acetyl-β-D-glucosaminidase (NAG), type IV collagen, TNF-α and 8-hydroxy-2'-deoxyguanosine (8-OHdG).

7. The miniature and intelligent urine sensing system as claimed in claim 1, wherein the miniature and intelligent urine sensing system conducts a message transmission with a cloud server database through the intelligent device to achieve an Internet of Things (loT) capable service, the cloud server database has a built-in artificial intelligence (AI) algorithm, which comprises: an early kidney disease risk assessment algorithm and a heart disease risk assessment algorithm, to calculate a degree of risk suffering from the heart disease based on concentrations of albumin, creatinine, cystatin C, NT-proBNP and troponin I in the urine detected by the urine signal detection device and assesses a risk of the heart disease and the kidney disease, as well as provides a result of a calculation or the assessment to medical personnel and users through an application of the intelligent device.

8. The miniature and intelligent urine sensing system as claimed in claim 1, wherein the miniature and intelligent urine sensing system conducts a message transmission with a cloud server database through the intelligent device to achieve an Internet of Things (loT) capable service, the cloud server database has a built-in artificial intelligence (AI) algorithm, which comprises: an early kidney disease risk assessment algorithm and a diabetes disease risk assessment algorithm, to calculate a degree of risk suffering from the diabetes disease based on a concentration in the urine of transferrin, N-acetyl-β-D-glucosaminidase (NAG), type IV collagen, TNF-α and 8 hydroxy-2'-deoxyguanosine (8-OHdG) detected by the urine signal detection device and assesses a risk of the diabetes disease and the kidney disease, as well as provides a result of a calculation or the assessment to medical personnel and users through an application of the intelligent device.

\* \* \* \* \*